United States Patent
Haas

(10) Patent No.: US 11,452,700 B2
(45) Date of Patent: Sep. 27, 2022

(54) METHOD OF DELIVERING AN ANESTHETIC AGENT AND GLUCOCORTICOID MICRO AND NANO BIOERODIBLE PARTICLES

(71) Applicant: Eric Haas, Houston, TX (US)

(72) Inventor: Eric Haas, Houston, TX (US)

(*) Notice: Subject to any disclaimer, the term of this patent is extended or adjusted under 35 U.S.C. 154(b) by 0 days.

(21) Appl. No.: 16/636,465

(22) PCT Filed: Aug. 3, 2018

(86) PCT No.: PCT/US2018/045151
§ 371 (c)(1),
(2) Date: Feb. 4, 2020

(87) PCT Pub. No.: WO2019/028339
PCT Pub. Date: Feb. 7, 2019

(65) Prior Publication Data
US 2020/0188338 A1 Jun. 18, 2020

Related U.S. Application Data

(60) Provisional application No. 62/541,167, filed on Aug. 4, 2017.

(51) Int. Cl.
*A61K 9/16* (2006.01)
*A61K 31/167* (2006.01)
*A61K 9/00* (2006.01)
*A61K 9/14* (2006.01)
*A61K 31/4458* (2006.01)

(52) U.S. Cl.
CPC .......... *A61K 31/167* (2013.01); *A61K 9/0024* (2013.01); *A61K 9/146* (2013.01); *A61K 9/1647* (2013.01); *A61K 31/4458* (2013.01)

(58) Field of Classification Search
CPC ...... A61K 31/167; A61K 9/0024; A61K 9/14; A61K 9/146; A61K 9/1647; A61K 31/4458; A61K 31/245; A61K 31/445; A61K 31/46; A61K 31/47; A61K 9/2022; A61K 9/167
See application file for complete search history.

(56) References Cited

U.S. PATENT DOCUMENTS

| | | | | |
|---|---|---|---|---|
| 5,700,485 | A * | 12/1997 | Berde | A61K 9/1641 424/426 |
| 2007/0248933 | A1 | 10/2007 | Rutherford et al. | |
| 2010/0086614 | A1 | 4/2010 | Junior et al. | |
| 2011/0027331 | A1* | 2/2011 | Hobot | A61K 9/5031 424/422 |

OTHER PUBLICATIONS

Search Report and Written Opinion for PCT/US2018/045151; dated Nov. 20, 2018; 10 pages.
International Preliminary Report on Patentability for PCT/US2018/045151; dated Feb. 4, 2020; 1 page.
Xu et al.; "Preparation of Monodisperse Biodegradable Polymer Microparticles Using a Microfluid Flow-focusing Device for Controlled Drug Delivery"; Small, vol. 5, No. 13; dated Jul. 2009; 13 pages.
Acharya et al.; "A study of drug release from homogeneous PLGA microstructures"; Journal of Controlled Release, vol. 146, pp. 201-206; dated Apr. 2010; 6 pages.
Shin et al.; "Application of Hydrogel Template Strategy in Ocular Drug Delivery"; Biomedical Nanotechnology: Methods and Protocols, Methods in Molecular Biology, vol. 1570, Chapter 19; 7 pages.
Acharya et al.; "Hydrogel Templates for the Fabrication of Homogeneous Polymer Microparticles"; Biomedical Nanotechnology: Methods and Protocols, Methods in Molecular Biology, vol. 726, Chapter 12; 7 pages.
Acharya et al.; "The hydrogel template method for fabrication of homogeneous nano/microparticles"; Journal of Controlled Release, vol. 141, pp. 314-319; dated Oct. 2009; 6 pages.

* cited by examiner

*Primary Examiner* — Carlos A Azpuru
(74) *Attorney, Agent, or Firm* — Morgan, Lewis & Bockius LLP

(57) ABSTRACT

The present disclosure provides polymeric particles and scaffolds comprising a matrix and an anesthetic agent. In one embodiment, the matrix comprises a bioerodible polymer. The disclosure further relates to the use of the polymeric particles and scaffolds for sustained local delivery of anesthetic agents, reduction of pain killer addiction and addiction risk. The disclosure also provides methods of fabricating and administering polymeric particles and scaffolds containing an anesthetic agent described herein.

6 Claims, No Drawings

US 11,452,700 B2

METHOD OF DELIVERING AN ANESTHETIC AGENT AND GLUCOCORTICOID MICRO AND NANO BIOERODIBLE PARTICLES

CROSS-REFERENCE TO RELATED APPLICATIONS

This application is a U.S. National Stage application of International Patent Application No. PCT/US2018/045151 filed Aug. 3, 2018, which claims the benefit of U.S. Provisional Patent Application No. 62/541,167 filed Aug. 4, 2017, all of which are incorporated by reference herein in their entireties.

GOVERNMENT LICENSE RIGHTS

This invention was made with government support under (identify the contract/grant No.) awarded by (identify the Federal agency). The government has certain rights in the invention.

FIELD OF THE INVENTION

This invention describes generally polymeric particles containing anesthetic agents, their use for sustained local delivery of anesthetic agents, reduction of pain killer addiction risk, and methods of fabricating and administering the polymeric particles containing anesthetic agents.

BACKGROUND OF THE INVENTION

In order to provide local or regional nerve blockade for extended periods and control pain, clinicians use local anesthetics administered through a catheter or syringe to a site where the pain is to be blocked. This requires repeated administration where the pain is to be blocked over a period of greater than one day, either as a bolus or through an indwelling catheter connected to an infusion pump. These methods have the disadvantage of potentially causing irreversible damage to nerves or surrounding tissues due to fluctuations in concentration and high levels of anesthetic. In addition, anesthetic administered by these methods are generally neither confined to the target area, nor delivered in a linear, continuous manner. In all cases, analgesia rarely lasts for longer than several hours.

Pain can also be controlled systemically by administration of pain killer drugs exhibiting opium or morphine-like properties generally referred to as opioids, or opioid agonists. However, repeated opioid use leads to potential development of tolerance, physical, anchor psychological dependence, i.e., addiction, which is a characteristic feature of most pain killer drugs containing opioid analgesics. Despite all attempts to diminish the potential for abuse, the misuse and abuse of opioid pharmaceutical products continues to increase, and there is a growing need for novel and effective methods and compositions to deter abuse of opioid pharmaceutical products.

SUMMARY OF THE INVENTION

In one embodiment, the invention relates to a drug delivery particle or scaffold including a polymer matrix and an anesthetic agent In some embodiments, the anesthetic agent is benzocaine, chloroprocaine, cyclomethycaine, dimethocaine, piperocaine, propoxycaine, procaine, proparacaine, tetracaine, articaine, bupivacaine, cinchocaine, etidocaine, levobupivacaine, lidocaine, mepivacaine, prilocaine, ropivacaine, or trimecaine. In one embodiment, the anesthetic agent is lidocaine. In one embodiment, the anesthetic agent is bupivacaine. In one embodiment, the anesthetic agent is ropivacaine. In some embodiments, the anesthetic agent is suspended or dissolved in the polymer matrix. In some embodiments, the polymer matrix includes a bioerodible polymer. In some embodiments, the polymer matrix includes a poly(alpha-hydroxy-acid) polymer or copolymer. In one embodiment, the polymer matrix includes a poly (lactic acid) polymer (PLA). In one embodiment, the polymer matrix includes a poly(glycolic acid) polymer (PGA). In one embodiment, the polymer matrix includes a poly(lactic-co-glycolic acid) polymer (PLGA). In one embodiment, the polymer matrix includes a poly(vinyl alcohol) polymer (PVA). In some embodiments, the size of the particle is less than 1 µm. In some embodiments, the drug delivery scaffold further includes a hydrogel.

In one embodiment, the invention relates to a method of delivering an anesthetic agent to a subject in need thereof, the method including administering to the subject one or more drug delivery particles, or a drug delivery scaffold. In some embodiments, the drug delivery particles, or the drug delivery scaffold, include a polymer matrix and an anesthetic agent. In some embodiments, the anesthetic agent is benzocaine, chloroprocaine, cyclomethycaine, dimethocaine, piperocaine, propoxycaine, procaine, proparacaine, tetracaine, articaine, bupivacaine, cinchocaine, etidocaine, levobupivacaine, lidocaine, mepivacaine, prilocaine, ropivacaine, or trimecaine. In some embodiments, after administration of the drug delivery particles, or of the drug delivery scaffold, the polymer matrix is gradually bioeroded and the anesthetic agent is sustainably released. In some embodiments, the anesthetic agent is sustainably released for between 1 hour and 6 hours, between 3 hours and 12 hours, between 9 hours and 24 hours, between 12 hours and 48 hours, between 1 day and 3 days. between 2 days and 1 week, between 1 week and 2 weeks, or longer than 2 weeks. In some embodiments, administration of the drug delivery particles or drug delivery scaffold is local. In some embodiments, administration of the drug delivery particles or drug delivery scaffold is parenteral. In some embodiments, administration of the drug delivery particles or drug delivery scaffold is intramuscular, intradermal, subcutaneous, or submucosal. In some embodiments, the anesthetic agent is sustainably released locally at or near the site of a wound or medical procedure.

In one embodiment, the invention relates to a method of reducing the dose of a pain killer prescribed to a subject in need thereof, the method including administering to the subject one or more drug delivery particles, or a drug delivery scaffold. In some embodiments, the drug delivery particles or the drug delivery scaffold include a polymer matrix and an anesthetic agent. In some embodiments, the anesthetic agent is benzocaine, chloroprocaine, cyclomethycaine, dimethocaine, piperocaine, propoxycaine, procaine, proparacaine, tetracaine, articaine, bupivacaine, cinchocaine, etidocaine, levobupivacaine, lidocaine, mepivacaine, prilocaine, ropivacaine, or trimecaine. In some embodiments, after administration of the drug delivery particles or the drug delivery scaffold, the polymer matrix is gradually bioeroded and the anesthetic agent is sustainably released. In some embodiments, the dose of pain killer is reduced by about 1%, about 2.5%, about 5%, about 7.5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, or about 100%. In some embodiments, the pain killer is an opioid. In some embodiments, the anesthetic agent is sustainably released for between 1 hour and 6 hours, between 3 hours and 12 hours, between 9 hours and 24 hours, between 12 hours and 48 hours, between 1 day and 3 days, between 2 days and 1 week, between 1 week and 2 weeks, or longer than 2 weeks. In some embodiments, administration of the drug delivery particles or drug delivery scaffold is local. In some embodiments, administration of the drug delivery particles or drug delivery scaffold is parenteral. In some embodiments, administration of the drug delivery particles or drug delivery scaffold is intramuscular, intradermal, subcutaneous, or submucosal. In some embodiments, the anesthetic agent is sustainably released locally at or near the site of a wound or medical procedure.

In one embodiment, the invention relates to a method of reducing addiction, or the risk of addiction, to a pain killer in a subject in need thereof, the method including administering to the subject one or more drug delivery particles, or a drug delivery scaffold. In some embodiments, the drug delivery particles, or the drug delivery scaffold, include a polymer matrix and an anesthetic agent. In some embodiments, the anesthetic agent is benzocaine, chloroprocaine, cyclomethycaine, dimethocaine, piperocaine, propoxycaine, procaine, proparacaine, tetracaine, articaine, bupivacaine, cinchocaine, etidocaine, levobupivacaine, lidocaine, mepivacaine, prilocaine, ropivacaine, or trimecaine. In some embodiments, after administration the polymer matrix is gradually bioeroded and the anesthetic agent is sustainably released. In some embodiments, the addiction, or the risk of addiction, to a pain killer is reduced by about 1%, about 2.5%, about 5%, about 7.5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, or about 100%, compared to the base line addiction or risk of addiction. In some embodiments, the base line addiction or risk of addiction is measured in the same subject, in a different subject, or in a population of subjects. In some embodiments, the pain killer is an opioid. In some embodiments, the anesthetic agent is sustainably released for between 1 hour and 6 hours, between 3 hours and 12 hours, between 9 hours and 24 hours, between 12 hours and 48 hours, between 1 day and 3 days, between 2 days and 1 week, between 1 week and 2 weeks, or longer than 2 weeks. In some embodiments, administration of the drug delivery particles or drug delivery scaffold is local. In some embodiments, administration of the drug delivery particles or drug delivery scaffold is parenteral. In some embodiments, administration of the drug delivery particles or drug delivery scaffold is intramuscular, intradermal, subcutaneous, or submucosal. In some embodiments, the anesthetic agent is sustainably released locally at or near the site of a wound or medical procedure.

In one embodiment, the invention relates to a method of forming drug delivery particles, or a drug delivery scaffold, the particles or the scaffold including a polymer matrix and an anesthetic agent, the method including the steps of providing a template having one or more recesses, and filing the recesses with a composition comprising the anesthetic agent. In some embodiments, the anesthetic agent is benzocaine, chloroprocaine, cyclomethycaine, dimethocaine, piperocaine, propoxycaine, procaine, proparacaine, tetracaine, articaine, bupivacaine, cinchocaine, etidocaine, levobupivacaine, lidocaine, mepivacaine, prilocaine, ropivacaine, or trimecaine. In some embodiments, a substantial portion of the composition filling a recess forms a drug delivery particle. In some embodiments, the method of forming drug delivery particles, or a drug delivery scaffold, further includes the step of separating the drug delivery particles from the template. In some embodiments, the template is dissolvable in a fluid, and the method further includes the steps of placing the template including formed drug delivery particles in an amount of fluid, dissolving the template, and collecting the drug delivery particles. In some embodiments, the template includes a hydrogel. In some embodiments, the hydrogel includes gelatin. In some embodiments, the template includes a poly(vinyl alcohol) polymer (PVA). In some embodiments, the polymer matrix includes a poly(lactic acid) polymer (PLA), a poly(glycolic acid) polymer (PGA), a polylactic-co-glycolic acid) polymer (PLGA), or a poly (vinyl alcohol) polymer (PVA).

DETAILED DESCRIPTION OF THE INVENTION

The invention relates generally to sustainable release drug delivery particles and scaffolds, and methods of making and using drug delivery particles and scaffolds. The particles and scaffolds disclosed include biodegradable and/or bioerodible polymers, which degrade once administered to a subject, while at the same time releasing the included drug. In some embodiments, at least 50% of the polymer degrades into residues, preferably non-toxic residues, which are subsequently removed by the body within a period of one week, two weeks, or the like. Polymers useful in the invention include polyanhydrides, polylactic acid-glycolic acid copolymers, polyorthoesters. In some embodiments, polylactic acid-glycolic acid copolymers are preferred. Local anesthetics are incorporated into the polymer using a method that yields a uniform dispersion, for example solubilization. Dispersion of a fine powder of anesthetic agent in the mass of the polymer can also be used. In some embodiments, sustained release can be attained not only by controlling the rate of polymer matrix bioerosion, but also by incorporation of a glucocorticoid into the polymeric matrix, or by co-administration of the glucocorticoid with the particles or scaffold.

Unless defined otherwise, all technical and scientific terms used herein have the same meaning as is commonly understood by one of skill in the art to which this invention belongs. All patents and publications referred to herein are incorporated by reference in their entireties.

Definitions

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., reduction of pain signaling). The specific dose will vary depending on the particular anesthetic agents and drug delivery particles or scaffolds chosen, the dosing regimen to be followed, whether the anesthetic agent is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, the terms "treat," "treatment," and/or "treating" may refer to the management of a disease, disorder, or pathological condition, risk thereof, or symptom thereof, with the intent to cure, ameliorate, stabilize, prevent, and/or control the disease, disorder, pathological condition, risk thereof, or symptom thereof. Regarding control of the disease, disorder, pathological condition, or risk thereof, more specifically, "control" may include the absence of condition progression, as assessed by the response to the methods recited herein, where such response may be complete (e.g., placing the disease in remission) or partial (e.g., lessening or ameliorating any symptoms associated with the condition).

The terms "QD," "qd," or "q.d." mean quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quater in die, four times a day, or four times daily.

The term "pharmaceutically acceptable salt" refers to salts derived from a variety of organic and inorganic counter ions known in the all. Pharmaceutically acceptable acid addition salts can be formed with inorganic acids and organic acids. Preferred inorganic acids from which salts can be derived include, for example, hydrochloric acid, hydrohromic acid, sulfuric acid, nitric acid, and phosphoric acid. Preferred organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum. Organic bases from which salts can be derived include, for example, primary, secondary, and tertiary amines, substituted amines including naturally occurring substituted amines, cyclic amines, and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

"Prodrug" is intended to describe a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers the advantages of solubility, tissue compatibility or delayed release in a mammalian organism (see, e.g., Bundgaard, H., Design of Prodrugs (1985) (Elsevier, Amsterdam). The term "prodrug" is also intended to include any covalently bonded carriers, which release the active compound in vivo when administered to a subject. Prodrugs of an active compound, as described herein, may be prepared by modifying functional groups present in the active compound in such a way that the modifications are cleaved, either in routine manipulation or in vivo, to yield the active parent compound. Prodrugs include, for example, compounds wherein a hydroxy, amino, or mercapto group is bonded to any group that, when the prodrug of the active compound is administered to a mammalian subject, cleaves to form a free hydroxy, free amino, or free mercapto group, respectively. Examples of prodrugs include, but are not limited to, acetates, formates, and benzoate derivatives of an alcohol, various ester derivatives of a carboxylic acid, or acetamide, formamide and benzamide derivatives of an amine functional group in the active compound.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}$C- or $^{14}$C-enriched carbons, are within the scope of this invention.

When ranges are used herein to describe, for example, physical or chemical properties such as, but not limited to, amounts, percentages, doses, molecular weights, or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation can be from 0% to 15%, from 0% to 10%, from 0% to 5%, or the like, of the stated number or numerical range.

The term "comprising," and related terms such as "comprise" or "comprises," or "having" or "including," includes those embodiments such as, for example, an embodiment of any composition of matter, method, or process that "consist of" or "consist essentially of" the described features.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Solvate" refers to a compound in physical association with one or more molecules of a pharmaceutically acceptable solvent.

Compounds included in the invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

Drug delivery particles and scaffolds of the present disclosure, including any of their ingredients, exhibit "biocompatibility" or are "biocompatible," meaning that the compositions are compatible with living tissue or a living system by not being substantially toxic, injurious, or physiologically reactive and not causing immunological rejection. The term "biocompatible" encompasses the terms "bioabsorbable," "bioresorbable," "biodegradable," and "bioerodible," which are defined herein.

Drug delivery particles and scaffolds of the present disclosure, including any of their ingredients, may be "bioabsorbable," "bioresorbable," "biodegradable," and/or bioerodible. As used herein, the terms "bioabsorbable" refers to materials or substances that dissipate upon implantation within a body, independent of which mechanisms by which dissipation can occur, such as dissolution, degradation, absorption, and excretion. As used herein, the term "bioresorbable" means capable of being absorbed by the body. As used herein, the terms "biodegradable" and/or "bioerodible" refer to materials which can decompose under physiological conditions into byproducts. Such physiological conditions include, for example, hydrolysis, i.e., decomposition via hydrolytic cleavage, enzymatic catalysis, or enzymatic degradation, mechanical interactions, and the like. As used herein, the term "biodegradable" also encompasses the term "bioresorbable", which describes a material or substance that decomposes under physiological conditions to break down to products that undergo bioresorption into the host-organism, namely, become metabolites of the biochemical systems of the host organism. As used herein, the terms "bioresorbable" and "bioresorption" encompass processes such as cell-mediated degradation, enzymatic degradation, hydrolytic degradation of the bioresorbable polymer, and/or elimination of the bioresorbable polymer from living tissue as will be appreciated by the person skilled in the art. The degree of biodegradation, bioabsorption, bioresorption, and/or bioerosion may be modified and/or controlled by, for example, adding one or more agents to compositions described herein that retard biodegradation, bioabsorption, bioresorption, and/or bioerosion. In addition, the degree of biodegradation, bioabsorption, bioresorption, and/or bioerosion may be modified and/or controlled by increasing or decreasing the degree of polymeric cross-linking present in the polymeric materials described herein. For example, the rate of biodegradation, bioabsorption, bioresorption, and/or bioerosion of the compositions described here may be increased by reducing the amount of crosslinking in the polymeric materials described herein. Alternatively, the rate of biodegradation, bioabsorption, bioresorption, and/or bioerosion of the drug delivery particles and scaffolds of the present disclosure, including any of their ingredients, described here, may be decreased by increasing the amount of crosslinking in the polymeric materials described herein.

For the avoidance of doubt, it is intended herein that particular features, e.g., integers, characteristics, values, uses, diseases, formulae, compounds, or groups described in conjunction with a particular aspect, embodiment, or example of the invention, are to be understood as applicable to any other aspect, embodiment or example described herein unless incompatible therewith. Thus such features may be used where appropriate in conjunction with any of the definition, claims or embodiments defined herein. All of the features disclosed in this specification (including any accompanying claims, abstract, and drawings), and/or all of the steps of any method or process so disclosed, may be combined in any combination, except combinations where at least some of the features and/or steps are mutually exclusive. The invention is not restricted to any details of any disclosed embodiments. The invention extends to any novel one, or novel combination, of the features disclosed in this specification (including any accompanying claims, abstract and drawings), or to any novel one, or any novel combination, of the steps of any method or process so disclosed.

Anesthetic Agents

Anesthetic agents useful in the invention are generally known in the art. The invention envisions however the use of any anesthetic agent, including anesthetic agents not yet known. In some embodiments, the anesthetics are local anesthetic, i.e., drugs which provide local numbness or pain relief. A number of different local anesthetics can be used, including benzocaine, chloroprocaine, cyclomethycaine, dimethocaine, piperocaine, propoxycaine, procaine, proparacaine, tetracaine, articaine, bupivacaine, cinchocaine, etidocaine, levobupivacaine, lidocaine, mepivacaine, prilocaine, ropivacaine, or trimecaine. In some embodiments, the local anesthetic is used the form of a salt, for example, the hydrochloride, bromide, acetate, citrate, or sulfate of the anesthetic agent. In some embodiments, compared to the free base form of these drugs, the more hydrophilic hydrochloride salt displays longer and denser nerve block, more complete release from polymer matrices, slower clearance from the targeted nerve area, and less encapsulation. Bupivacaine is a long acting and potent local anesthetic, providing other advantages such as sufficient sensory anesthesia without significant motor blockage, lower toxicity, and wide availability.

In some embodiments, the anesthetic agent is an ester group anesthetic agent, for example, benzocaine, chloroprocaine, cyclomethycaine, dimethocaine (larocaine), piperocaine, propoxycaine, procaine (novocaine), proparacaine, or tetracaine (amethocaine). Representative examples of ester group anesthetic agents are listed in Table 1.

TABLE 1

Ester Group Anesthetic Agents

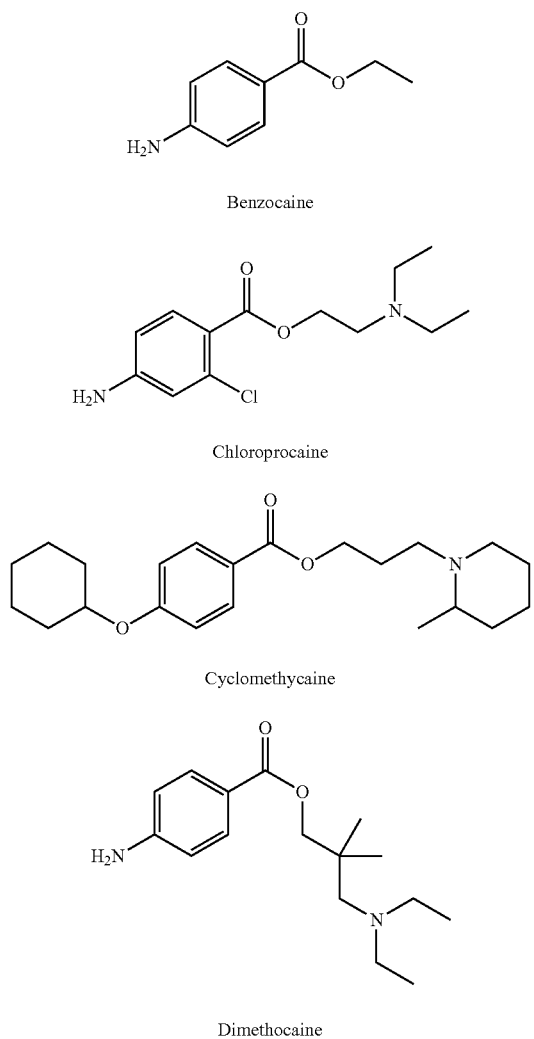

TABLE 1-continued

Ester Group Anesthetic Agents

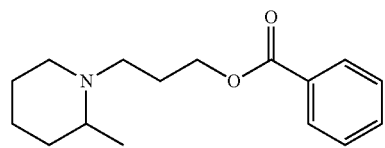 [SMILES: CC1CCCCN1CCCOC(=O)c1ccccc1]

Piperocaine

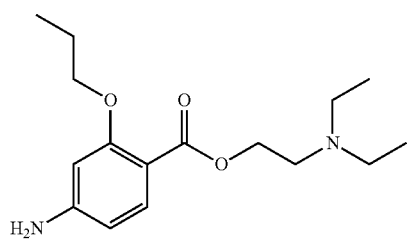 [SMILES: CCCOc1cc(N)ccc1C(=O)OCCN(CC)CC]

Propoxycaine

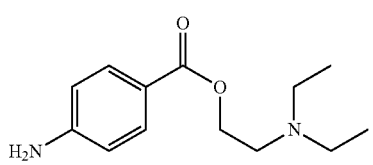 [SMILES: CCN(CC)CCOC(=O)c1ccc(N)cc1]

Procaine

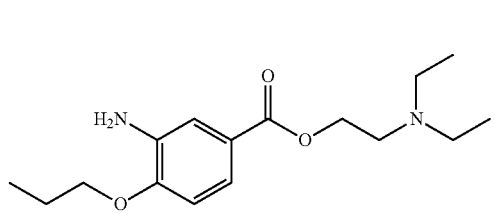 [SMILES: CCCOc1ccc(C(=O)OCCN(CC)CC)cc1N]

Proxymetacaine

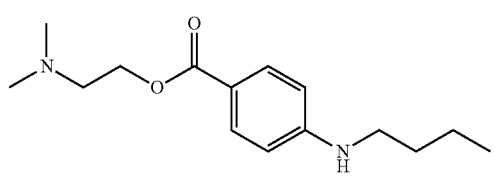 [SMILES: CCCCNc1ccc(C(=O)OCCN(C)C)cc1]

Tetracaine

In some embodiments, the anesthetic agent is an amide group anesthetic agent, for example, articaine, bupivacaine, cinchocaine (dibucaine), etidocaine, levobupivacaine, lidocaine (lignocaine), mepivacaine, prilocaine, ropivacaine, or trimecaine. Representative examples of amide group anesthetic agents are listed in Table 2.

TABLE 2

Amide Group Anesthetic Agents

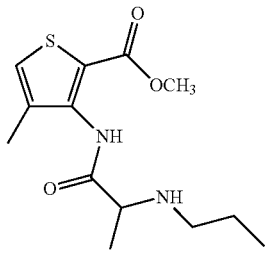 [SMILES: CCCNC(C)C(=O)Nc1c(C)csc1C(=O)OC]

Articaine

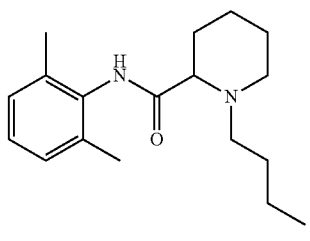 [SMILES: CCCCN1CCCCC1C(=O)Nc1c(C)cccc1C]

Bupivacaine

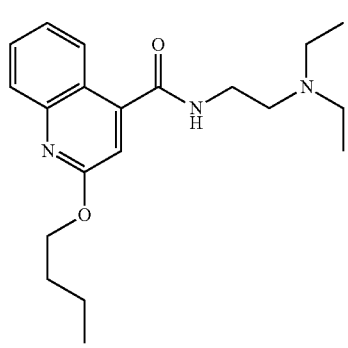 [SMILES: CCCCOc1cc(C(=O)NCCN(CC)CC)c2ccccc2n1]

Cinchocaine

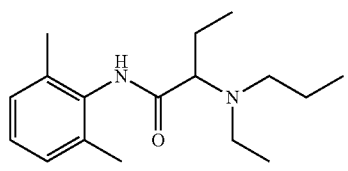 [SMILES: CCCN(CC)C(CC)C(=O)Nc1c(C)cccc1C]

Etidocaine

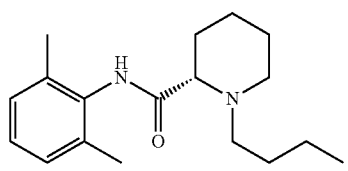 [SMILES: CCCCN1CCCC[C@H]1C(=O)Nc1c(C)cccc1C]

Levobupivacaine

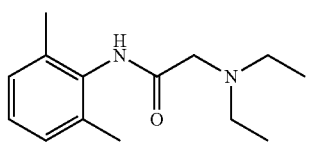 [SMILES: CCN(CC)CC(=O)Nc1c(C)cccc1C]

Lidocaine

TABLE 2-continued

Amide Group Anesthetic Agents

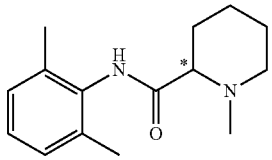 [SMILES: Cc1cccc(C)c1NC(=O)C1CCCCN1C]

Mepivacaine

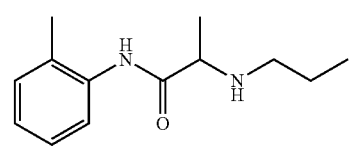 [SMILES: CCCNC(C)C(=O)Nc1ccccc1C]

Prilocaine

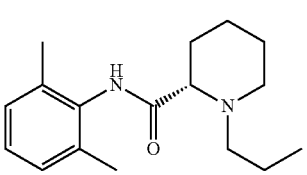 [SMILES: CCCN1CCCC[C@H]1C(=O)Nc1c(C)cccc1C]

Ropivacaine

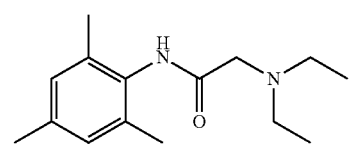 [SMILES: CCN(CC)CC(=O)Nc1c(C)cc(C)cc1C]

Trimecaine

Polymer Matrix

The polymers used to make the particles and scaffolds of the invention are for example polyanhydrides, polylactic acid-glycolic acid copolymers, or polyorthoesters. In some embodiments, the polymer matrix includes a poly(alpha-hydroxy-acid) polymer or copolymer. In one embodiment, the polymer matrix includes a polylactic acid) polymer (PLA). In one embodiment, the polymer matrix includes a poly(glycolic acid) polymer (PGA). In one embodiment, the polymer matrix includes a polylactic-co-glycolic acid) polymer (PLEA). In one embodiment, the polymer matrix includes a poly(vinyl alcohol) polymer (PVA). The polymers used are biodegradable and bioerodible. In some embodiments, polylactic acid-glycolic acid copolymers are preferred.

The polymers used are generally biocompatible. The polymers used degrade in vivo over a period of less than a year, with at least 50% of the polymer degrading within six months or less. More preferably, the polymer will degrade significantly within a month, with at least 50% of the polymer degrading into non-toxic residues which are removed by the body, and 100% of the drug being released within a certain period of time, for example between 1 hour and 6 hours, between 3 hours and 12 hours, between 9 hours and 24 hours, between 12 hours and 48 hours, between 1 day and 3 days, between 2 days and 1 week, between 1 week and 2 weeks, or longer than 2 weeks.

Polymers degrade by hydrolysis, by surface erosion, or by bulk erosion. In some embodiments, surface erosion is preferred, as it affords not only a sustained drug release, but also a release which is, in some embodiments, linear or quasi-linear.

When using a poly(lactic-co-glycolic acid) polymer (PLGA), the weight ratio of lactic acid to glycolic acid can be adjusted to achieve various end parameters. In some embodiments, the weight ratio of lactic acid to glycolic acid is between about 99:1 to about 1:99, between about 95:5 to about 5:95, between about 90:10 to about 10:90, between about 75:25 to about 25:75, between about 65:35 to about 35:65, or between about 55:45 to about 45:55. In some embodiments, the w/w ratio between lactic acid to glycolic acid is between about 99:1 to about 55:45, between about 95:5 to about 45:55, between about 90:10 to about 35:65, between about 75:25 to about 15:85, between about 65:35 to about 10:90, or between about 55:45 to about 1:99. In an embodiment, the weight ratio of lactic acid to glycolic acid is about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, about 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89, about 10:90, about 9:91, about 8:92, about 7:93, about 6:94, about 5:95, about 4:96, about 3:97, about 2:98, or about 1:99. In some embodiments, the weight ratio of lactic acid to glycolic acid is no more than 4:1 (i.e., 80% or less lactic acid to 20% or more glycolic acid by weight). Other polymers include protein polymers such as gelatin and fibrin, and polysaccharides such as chitosan and/or hyaluronic acid.

Methods of Making

In some embodiments, the drug delivery particles and scaffolds can be made using the hydrogel template method, and/or the PVA template method. The methods are described in: Acharya et al., 2010, Journal of Controlled Release, 146, 201-206; Shin et al., Biomedical Nanotechnolony: Methods and Protocols, Methods in Molecular Biology, vol. 1570, Chapter 19, DOI 10.1007/978-1-4939-6840-4_19; Acharya et al., Biomedical Nanotechnology: Methods and Protocols, Methods in Molecular Biology, vol. 726. Chapter 12. DOI 10.1007/978-1-61779-052-2_12, and Acharya et al., 2010, Journal of Controlled Release, 141, 314-319; incorporated in their entireties herein.

In some embodiments, the methods of making e drug delivers particles and scaffolds of the invention rely on the use of template including a substantially flat surface decorated with a series of protuberances. The protuberances serve as shaping sub-templates for the final shape and size of the drug delivery particles. In some embodiments, the template can be made from a silicon polymer, and the protuberances can have various shapes, e.g., cylindrical, prismatic, conical, and the like. The protuberances can be sized on a nano scale or on a micro scale, and can have a height from tens or hundreds of nanometers, to tens or hundreds of micrometers. The protuberances can have dimensions on the three axis of space, for example a diameter or a sectional axis, similarly sized to the height, i.e., from tens or hundreds of nanometers, to tens or hundreds of micrometers. In one embodiment, the protuberances are cylindrical. In some embodiments, the template is flexible. In some embodiments, the template is made from a silicon based polymer.

In some embodiments, a solution, a suspension, or a gel including a polymer, can be casted or poured onto the template. In some embodiments, the polymer can be a mixture of proteins, for example gelatin or fibrin. In some embodiments, the polymer can be PVA. Under various conditions described in the art, the polymer, for example gelatin or PVA, coalesces to form a scaffold which can thereafter be removed from the template. The concentration of the solution can be adjusted in order to afford a scaffold with various degrees of elasticity and mechanical strength. Once coalesced, the scaffold is removed, for example peeled, from the template. The scaffold is shaped as the negative image of the template. For example, if the template includes cylindrical protuberances, the scaffold includes cylindrical recesses. The size of the scaffold recesses substantially mirrors the size of the template protuberances. The recesses are sized on a nano scale or on a micro scale, and have a depth from tens or hundreds of nanometers, to tens or hundreds of micrometers. The recesses have dimensions on the three axis of space, for example a diameter or a sectional axis, from tens or hundreds of nanometers, to tens or hundreds of micrometers. In one embodiment, the recesses are cylindrical.

In some embodiments, the depth of the scaffold recesses is from about 2.50 nm to about 500 nm, from about 450 nm to about 750 nm, from about 650 nm to about 1 µm, from about 850 nm to about 2.5 µm, from about 1 µm to about 10 µm, from about 5 µm to about 75 µm, from about 50 µm to about 250 µm, from about 100 µm to about 500 µm, from about 450 µm to about 750 µm, or from about 500 µm to about 1 mm.

In some embodiments, the diameter of the scaffold recesses is from about 250 nm to about 500 nm, from about 450 nm to about 750 nm, from about 650 nm to about 1 µm, from about 850 nm to about 2.5 µm, from about 1 µm to about 10 µm, from about 5 µm to about 75 µm, from about 50 µm to about 250 µm from about 100 µm to about 500 µm, from about 450 µm to about 750 µm, or from about 500 µm to about 1 mm.

In some embodiments, any end to end dimension of the scaffold recesses is from about 250 nm to about 500 nm, from about 450 nm to about 750 nm, from about 650 nm to about 1 µm, from about 850 nm to about 2.5 µm, from about 1 µm to about 10 µm, from about 5 µm to about 75 µm, from about 50 µm to about 250 µm, from about 100 µm to about 500 µm, from about 450 µm to about 750 µm, or from about 500 µm to about 1 mm.

The scaffold recesses are thereafter filled with a composition including an anesthetic agent. The composition can be a solution, a suspension, a gel, or the like. The anesthetic agent composition is cast, poured, or otherwise dispose on the side of the scaffold having recesses, and the excess composition is removed by various methods, for example by a doctor blade device. The composition may include a solvent, and/or a polymer. In some embodiments, the polymer can be the same polymer as used in the scaffold. In some embodiments, the polymer can be different than the polymer used in the scaffold. In some embodiments, the polymer in the composition includes a polyalpha-hydroxy-acid) polymer or copolymer. In one embodiment, the polymer in the composition includes a polylactic acid) polymer (PLA). In one embodiment, the polymer in the composition includes a poly(glycolic acid) polymer (PGA). In one embodiment, the polymer in the composition includes a poly(lactic-co-glycolic acid) polymer (PLGA). In one embodiment, the polymer in the composition includes a poly(vinyl alcohol) polymer (PVA). In some embodiments, the composition includes a protein mixture, for example gelatin of fibrin. The composition generally coalesces to fill a substantial portion of the totality of scaffold recesses with a particle including the anesthetic agent. The scaffold having a substantially portion of the totality of recesses substantially filled with particles including an anesthetic agent can be used as such. The scaffold can for example be cut into a particular shape and/or size, and used as an implant. In one embodiment, the scaffold can be cut into circular, square, triangular, trapezoidal, rectangular, or the like, patches.

In some embodiments, the materials in the scaffold are generally able to dissolve, While the materials in the scaffold recesses, i.e., the materials making a particle, are not, or have a lesser degree of solvability than the scaffold material. Thus the scaffold can be submerged into various solutions known in the art, where the majority of the materials making the scaffold dissolve, leaving the particles in the scaffold recesses undissolved. The particles are thereafter collected as a multitude of drug delivery particles including a polymer matrix and an anesthetic agent. The resulting particles are obtained in a variety of shapes, for example cylindrical, prismatic, or the like. The resulting particles are obtained in a variety of sizes, depending on the size of the protuberances and recesses described here relative to the making of the drug delivery particles. The particles may be generally consistent in size or may be part of a distribution (e.g., formed from an emulsion). In some embodiments, any end to end dimension of the particles is from about 250 nm to about 500 nm, from about 450 nm to about 750 nm, from about 650 nm to about 1 µm, from about 850 nm to about 2.5 µm, from about 1 µm to about 10 µm, from about 5 µm to about 75 µm, from about 50 µm to about 250 µm, from about 100 µm to about 500 µm, from about 450 µm to about 750 µm, or from about 500 µm to about 1 mm. In some embodiments, any transversal, axial, or otherwise end to end dimension of the particles is about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, or about 1 µm. In some embodiments, any transversal, axial, or otherwise end to end dimension of the particles is about 50 µm, about 100 µm, about 150 µm, about 200 µm, about 250 µm, about 300 µm, about 350 µm, about 400 µm, about 450 µm, about 500 µm, about 550 µm, about 600 µm, about 650 µm, about 700 µm, about 750 µm, about 800 µm, about 850 µm, about 900 µm, about 950 µm, or about 1 mm.

Pharmaceutical Compositions

In one embodiment, the invention provides a pharmaceutical composition for use in the treatment of the diseases and conditions described herein. In a preferred embodiment, the invention provides pharmaceutical compositions, including those described below, for use in the treatment of pain, by local administration. In some embodiments, the invention relates to a pharmaceutical composition including one or more anesthetic agents, or pharmaceutically acceptable salts, solvates, hydrates, cocrystals, or prodrugs thereof. In some embodiments, the anesthetic agent is formulated into a drug delivery particle, or a drug delivery scaffold. In some embodiments, the pharmaceutical compositions further include a physiologically compatible carrier medium.

The pharmaceutical compositions are typically formulated to provide a therapeutically effective amount of an anesthetic agent, or a fragment, derivative, conjugate, variant, radioisotope-labeled complex, or biosimilar thereof, or pharmaceutically acceptable salts, prodrugs, solvates, or hydrates thereof, as the active ingredients. Where desired, the pharmaceutical compositions contain a pharmaceutically acceptable salt and/or coordination complex of one or more of the active ingredients. Typically, the pharmaceutical compositions also comprise one or more pharmaceutically acceptable excipients, carriers, including inert solid diluents and fillers, diluents, including sterile aqueous solution and various organic solvents, permeation enhancers, solubilizers and adjuvants.

In some embodiments, the concentration of any one anesthetic agent provided in a pharmaceutical composition of the invention, for example in a drug delivery particle or a drug delivery scaffold, is independently less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v of the pharmaceutical composition.

In some embodiments, the concentration of any one anesthetic agent provided in a pharmaceutical composition of the invention, for example in a drug delivery particle or a drug delivery scaffold, is independently greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%. 0.0004%, 0.0003%, 0.0002%, or 0.0001% w/w, w/v, or v/v of the pharmaceutical composition.

In some embodiments, the concentration of any one anesthetic agent provided in a pharmaceutical composition of the invention, for example in a drug delivery particle or a drug delivery scaffold, is independently in the range from about 0.0001% to about 50%, from about 0.001%) to about 40%, from about 0.01% to about 30%, from about 0.02% to about 29%, from about 0.03% to about 28%, from about 0.04% to about 27%, from about 0.05% to about 26%, from about 0.0600 to about 25%, from about 0.07% to about 24%, from about 0.08% to about 23%, from about 0.09% to about 22%, from about 0.1% to about 21%, from about 0.2% to about 20%, from about 0.3% to about 19%, from about 0.4% to about 18%, from about 0.5% to about 17%, from about 0.6% to about 16%, from about 0.70 to about 15%, from about 0.8% to about 14%, from about 0.9% to about 12%, or from about 1% to about 10% w/w, w/V, or v/v of the pharmaceutical composition.

In some embodiments, the concentration of any one anesthetic agent provided in a pharmaceutical composition of the invention, for example in a drug delivery particle or in a drug delivery scaffold, is independently in the range from about 0.001% to about 10%, from about 0.01% to about 5%, from about 0.02% to about 4.5%, from about 0.03% to about 4%, from about 0.04% to about 3.5%, from about 0.05% to about 3%, from about 0.06% to about 2.5%, from about 0.07% to about 2%, from about 0.08% to about 1.5%, from about 0.09% to about 1%, from about 0.1% to about 0.9% w/w, w/v or v/v of the pharmaceutical composition.

In some embodiments, the amount of anesthetic agent provided in a pharmaceutical composition of the invention, for example in a dose including drug delivery particles, or drug delivery scaffold, is independently equal to or less than about 10 g, about 9.5 g, about 9.0 g, about 8.5 g, about 8.0 g. about 7.5 g, about 7.0 g, about 6.5 g, about 6.0 g, about 5.5 g, about 5.0 g, about 4.5 g, about 4.0 g, about 3.5 g. about 3.0 g, about 2.5 g, about 2.0 g, about 1.5 g, about 1.0 g, about 0.95 g, about 0.9 g, about 0.85 g, about 0.8 g, about 0.75 g, about 0.7 g, about 0.65 g, about 0.6 g, about 0.55 g, about 0.5 g, about 0.45 g, about 0.4 g, about 0.35 g, about 0.3 g, about 0.25 g, about 0.2 g, about 0.15 g, about 0.1 g, about 0.09 g, about 0.08 g, about 007 g, about 0.06 g, about 0.05 g, about 0.04 g, about 0.03 g, about 0.02 g, about 0.01 g, about 0,009 g, about 0,008 g, about 0.007 g, about 0.006 g, about 0.005 g, about 0.004 g, about 0.003 g, about 0.002 g, about 0.001 g, about 0.0009 g, about 0.0008 g, about 0.0007 g, about 0.0006 g, about 0.0005 g, about 0.0004 g, about 0.0003 g, about 0.0002 g, or about 0.0001 g.

Pharmaceutical Compositions for Injection

In preferred embodiments, the invention provides a pharmaceutical composition for injection containing drug delivery particles or drug delivery scaffolds according to the invention, and a pharmaceutical excipient suitable for injection. Components and amounts of agents in the compositions are as described herein. The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, and thimerosal.

Sterile injectable solutions are prepared by incorporating drug delivery particles or drug delivery scaffolds including an anesthetic agent described here, in the required amounts, in the appropriate solvent with various other ingredients as enumerated above, as required, followed by sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical compositions may also be prepared from compositions described herein and one or more pharmaceutically acceptable excipients suitable for intraosseous, intraocular, epidural, or intraspinal administration. Preparations for such pharmaceutical compositions are well-known in the art. See, e.g., Anderson, et al., eds., Handbook of Clinical Drug Data, Tenth Edition, McGraw-Hill, 2002; and Pratt and Taylor, eds., Principles of Drug Action, Third Edition, Churchill Livingston, N.Y., 1990, each of which is incorporated by reference herein in its entirety.

Methods of Treatment

The drug delivery particles and scaffolds of the invention are used in any therapeutic indication requiring pain management. Traumatic injuries, whether accidental or as a result of a medical procedure, can be accordingly treated by using the drug delivery particles or scaffolds described here. When placed, for example injected, at or near the site of a an injury, for example a cut, laceration, or surgical incision, the drug delivery particles and scaffolds of the invention are designed to biodegrade and sustainably deliver the anesthetic agent included. The anesthetic agent is sustainably released for between 1 hour and 6 hours, between 3 hours and 12 hours, between 9 hours and 24 hours, between 12 hours and 48 hours, between 1 day and 3 days, between 2 days and 1 week, between 1 week and 2 weeks, or longer than 2 weeks. In some embodiments, the anesthetic agent is sustainably released for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In some embodiments, the anesthetic agent is sustainably released for about 1 day, about 2 days, about 3 days, about 4 days, about 5 days, about 6 days, about 7 days, about 8 days, about 9 days, about 10 days, about 11 days, about 12 days, about 13 days, or about 14 days. In some embodiments, the anesthetic agent is sustainably released for about 1 week, about 2 weeks, about 3 weeks, about 4 weeks, about 5 weeks, about 6 weeks, about 7 weeks, or about 8 weeks. In some embodiments, the anesthetic agent is sustainably released for a period of time including any combination of hours, days, and/or weeks described here.

By sustainably releasing one or more anesthetic agents, the drug delivery particles and scaffolds described here afford a better pain management system, and thus result in a decrease, and in some embodiments, a complete elimination for the need of systemic pain medication. For example, even if the practitioner still prescribes systemic pain medication, for example an opioid, the drug delivery particles and scaffolds described here afford a reduction in the dose of pain killer prescribed to the subject or patient in need thereof. In some embodiments, the dose of pain killer is reduced by about 1%, about 2.5%, about 5%, about 7.5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, or about 100%. In some embodiments, the dose of pain killer is reduced by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 590, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%, in some embodiments, the dose of pain killer is completely eliminated. In some embodiments, the pain killer is an opioid.

By reducing the dose of pain medication needed or required, the use of drug delivery particles and scaffolds described here result in a reduction of any existing addiction to a pain killer, or a reduction in the risk of acquiring such addiction. In some embodiments, the pain killer is an opioid. In some embodiments, the addiction, or the risk of addiction, to a pain killer is reduced by about 1%, about 2.5%, about 5%, about 7.5%, about 10%, about 15%, about 20%, about 25%, about 30%, about 359%, about 40%, about 45%, about 50%, about 55%, about 60%, about 65%, about 70%, about 75%, about 80%, about 85%, about 90%, about 95%, about 99%, or about 100%, compared to the base line addiction or risk of addiction. In some embodiments, the addiction, or the risk of addiction, to a pain killer is reduced by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%, compared to the base line addiction or risk of addiction. The base line addiction or risk of addiction is measured in the same subject, in a different subject, or in a population of subjects.

Methods of Administration

Administration of a composition including drug delivery particles or drug delivery scaffolds according to the invention, can be effected by any method that enables delivery of the compounds to the site of action. These methods include parenteral injection (including subcutaneous, submucosal, intramuscular, intravascular, intraperitoneal, or infusion), topical (e.g., transdermal application), rectal administration, via local delivery by catheter or stent. The compositions thereof can also be administered intraadiposally or intrathecally. Exemplary parenteral administration forms include solutions or suspensions of active compound in sterile aqueous solutions, for example, aqueous propylene glycol or dextrose solutions. Such dosage forms can be suitably buffered, if desired.

In some embodiments, formulations including the drug delivery particles and scaffolds described herein are locally administered, for example by injection or implantation, at or near the site of a wound or surgical procedure. Methods and protocols for determining the best location for local delivery are known in the art.

The invention also provides kits. The kits include drug delivery particles or drug delivery scaffolds according to the invention, or pharmaceutical compositions thereof, either alone or in combination, in suitable packaging, and written material that can include instructions for use, discussion of clinical studies, and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient.

Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

In some embodiments, the invention provides a kit comprising a composition comprising a therapeutically effective amount of anesthetic agents, as formulated into drug delivery particles or scaffolds, according to the invention, or anesthetic agents, conjugates, variants, radioisotope-labeled complexes, pharmaceutically acceptable salts, solvates, hydrates, cocrystals, or prodrugs thereof, similarly formulated into drug delivery particles or scaffolds described here. These compositions are typically pharmaceutical compositions.

The kits described above are preferably for use in the treatment of the diseases and conditions described herein. In a preferred embodiment, the kits are for use in the treatment of pain, or in the treatment of pain medication addiction or risk of acquiring addiction.

Combinations of Anesthetic Agents with Other Active Pharmaceutical Ingredients

The anesthetic agents described here, including the drug delivery particles and scaffolds described here, can also be co-administered with additional chemotherapeutic active pharmaceutical ingredients, for example anti-inflammatories such as glucocorticoids, that are useful to prolong in vivo sustainable release. Glucocorticoids include dexamethasone, cortisone, prednisone, and others routinely administered orally, or by injection. Useful loadings are from 0.01 to 30% by weight, preferably between 0.05 and 0.5%. The dosage must be low enough to avoid toxicity. Glucocorticoids such as dexamethasone prolong release in vivo, and do not reduce the intensity of the nerve block generated by the release of the anesthetic agent from the polymer, and do not affect the recovery of sensation and strength.

While preferred embodiments of the invention are shown and described herein, such embodiments are provided by way of example only and are not intended to otherwise limit the scope of the invention. Various alternatives to the described embodiments of the invention may be employed in practicing the invention.

The invention claimed is:

1. A method of delivering an anesthetic agent to a subject in need thereof, comprising administering to the subject one or more drug delivery particles, or a drug delivery scaffold, comprising a polymer matrix and an anesthetic agent selected from the group consisting of benzocaine, chloroprocaine, cyclomethycaine, dimethocaine, piperocaine, propoxycaine, procaine, proparacaine, tetracaine, articaine, bupivacaine, cinchocaine, etidocaine, levobupivacaine, lidocaine, mepivacaine, prilocaine, ropivacaine, and trimecaine, wherein after administration the polymer matrix is gradually bioeroded and the anesthetic agent is sustainably released, and wherein the drug delivery particles or drug delivery scaffold further comprises 0.01 to 30% by weight of a glucocorticoid or wherein 0.01 to 30% by weight of a glucocorticoid is co-administered to the subject with the drug delivery particles or drug delivery scaffold.

2. The method of claim 1, wherein the anesthetic agent is sustainably released for between 1 hour and 6 hours, between 3 hours and 12 hours, between 9 hours and 24 hours, between 12 hours and 48 hours, between 1 day and 3 days, between 2 days and 1 week, between 1 week and 2 weeks, about 2 weeks, about 3 weeks, about 4 weeks, about 5 weeks, about 6 weeks, about 7 weeks, or about 8 weeks.

3. The method of claim 1, wherein administration is local.

4. The method of claim 1, wherein administration is parenteral.

5. The method of claim 1, wherein administration is intramuscular, intradermal, subcutaneous, or submucosal.

6. The method of claim 1, wherein the anesthetic agent is sustainably released locally at or near the site of a wound or medical procedure.

* * * * *